United States Patent
Fournier

(10) Patent No.: US 9,839,362 B2
(45) Date of Patent: Dec. 12, 2017

(54) DEVICE AND METHOD FOR COMBINED CONTINUOUS NON-INVASIVE MEASUREMENT OF BLOOD PRESSURE AND PULSE OXIMETRY (SPO2)

(75) Inventor: Donald Fournier, Georgetown, MA (US)

(73) Assignee: Draeger Medical Systems, Inc., Andover, MA (US)

( * ) Notice: Subject to any disclaimer, the term of this patent is extended or adjusted under 35 U.S.C. 154(b) by 490 days.

(21) Appl. No.: 13/995,348

(22) PCT Filed: Dec. 12, 2011

(86) PCT No.: PCT/US2011/064416
§ 371 (c)(1),
(2), (4) Date: Jun. 18, 2013

(87) PCT Pub. No.: WO2012/087634
PCT Pub. Date: Jun. 28, 2012

(65) Prior Publication Data
US 2014/0114152 A1 Apr. 24, 2014

Related U.S. Application Data

(60) Provisional application No. 61/426,679, filed on Dec. 23, 2010.

(51) Int. Cl.
*A61B 5/1455* (2006.01)
*A61B 5/0205* (2006.01)
(Continued)

(52) U.S. Cl.
CPC ........ *A61B 5/0205* (2013.01); *A61B 5/02116* (2013.01); *A61B 5/02241* (2013.01);
(Continued)

(58) Field of Classification Search
CPC .................................................. A61B 5/1455
See application file for complete search history.

(56) References Cited

U.S. PATENT DOCUMENTS

| | | |
|---|---|---|
| 5,309,916 A | 5/1994 | Hatschek |
| 2004/0092832 A1 | 5/2004 | Schnall et al. |

(Continued)

FOREIGN PATENT DOCUMENTS

| | | |
|---|---|---|
| EP | 0 444 934 A1 | 9/1991 |
| EP | 0 467 853 A1 | 1/1992 |

(Continued)

*Primary Examiner* — Eric Winakur
*Assistant Examiner* — Marjan Fardanesh
(74) *Attorney, Agent, or Firm* — Jones Day

(57) ABSTRACT

An apparatus and method for measuring at least two patient parameters is provided. A first cuff includes a first inflatable bladder, a first light emitting device and a first sensor that senses light data for use in calculating at least two patient parameters. A second cuff includes a second inflatable bladder, a second light emitting device and a second sensor that senses light data for use in calculating the at least two patient parameters. A controller is coupled the first and second sensors and when the controller causes the bladder of one of the first and second cuffs to inflate, the sensor of the one of the first and second cuffs sensing first light data used in determining a first of the at least two patient parameters and the sensor of the other of the one of first and second cuffs simultaneously senses second light data used in determining of a second of the at least two patient parameters.

26 Claims, 6 Drawing Sheets

(51) Int. Cl.
    *A61B 5/021*     (2006.01)
    *A61B 5/022*     (2006.01)
    *A61B 5/00*     (2006.01)

(52) U.S. Cl.
    CPC ........ *A61B 5/14552* (2013.01); *A61B 5/6826* (2013.01); *A61B 5/6843* (2013.01); *A61B 2562/043* (2013.01)

(56) References Cited

U.S. PATENT DOCUMENTS

2006/0074283 A1     4/2006    Henderson et al.
2006/0195034 A1     8/2006    Skrabal et al.

FOREIGN PATENT DOCUMENTS

WO     WO/2000/59369     10/2000
WO     WO/2008/071643     6/2008

DEVICE AND METHOD FOR COMBINED CONTINUOUS NON-INVASIVE MEASUREMENT OF BLOOD PRESSURE AND PULSE OXIMETRY (SPO2)

CROSS REFERENCE TO RELATED APPLICATIONS

This application is a National Stage Application under 35 U.S.C. 371 of PCT application PCT/2011/064416, filed Dec. 12, 2011 which claims priority from U.S. Provisional Patent Application Ser. No. 61/426,679 filed on Dec. 23, 2010 by Donald Fournier. The disclosures of the aforementioned applications are hereby incorporated by reference herein in their entireties.

FIELD OF THE INVENTION

The present invention relates to a finger cuff that integrates an SpO2 sensor with a continuous, non-invasive, arterial blood pressure (CNAP) sensor for non-invasively determining arterial blood pressure and the level of oxygen saturation in blood from a single device.

BACKGROUND OF THE INVENTION

The "vascular unloading technique" or "volume-clamp method" introduced by Peñaz in the early 1970's provided for a new method to continuously and non-invasively monitor arterial blood pressure (CNAP). Devices exist that include a band that is externally placed over adjacent fingers containing arteries of comparable size. A sensor detects pulsating changes in the arteries based on the amount of light transmitted through the tissue. The transmitted light intensity is used to measure the blood volume under the finger artery. The pressure in the cuff is changed by compression and decompression to keep the blood volume substantially constant. By maintaining a constant blood volume, the arterial wall is relaxed and the cuff pressure is substantially identical to the pressure in the underlying artery. The cuff pressure therefore reflects the intra-arterial pressure under the finger cuff and continuous non-invasive beat-to-beat pressures can be calculated.

In addition to continuous non-invasive blood pressure measurements, obtaining information regarding the blood oxygen saturation level of a patient using a non-invasive monitoring mechanism is desirable in both diagnosis and treatment of medical conditions. Blood oxygen saturation level may be determined using a technique known as transmission spectrophotometry, or more widely known as pulse oximetry (SpO2). Conventionally, pulse oximetry measurements are obtained via a sensor positioned on a finger of the hand having the non-invasive blood pressure monitor connected thereto or on a finger on the contra-lateral hand. A drawback associated with this configuration is increased discomfort to the patient and an increase in the number of sensors connected to the patient making monitoring more costly and cable management more difficult for healthcare professionals. A further drawback is the increased chance that one or more sensors would become dislodged thereby disrupting patient monitoring.

Accordingly, there is a need for a device and a method that permits simultaneous CNAP and SpO2 measurements without increasing the number of separate sensors attached to a patient. In addition, it would also be desirable to provide a cuff design adaptable to the patient's finger circumference, thereby reducing measurement errors related to cuff application and cuff shifting on the finger. A system according to invention principles addresses deficiencies of known systems.

SUMMARY OF THE INVENTION

In one embodiment, an apparatus for measuring at least two patient parameters is provided. A first cuff includes a first inflatable bladder, a first light emitting device and a first sensor that senses light data for use in calculating at least two patient parameters. A second cuff includes a second inflatable bladder, a second light emitting device and a second sensor that senses light data for use in calculating the at least two patient parameters. A controller is coupled to the first and second sensors and when the controller causes the bladder of one of the first and second cuffs to inflate, the sensor of the one of the first and second cuffs senses first light data used in determining a first of the at least two patient parameters and the sensor of the other of the one of first and second cuffs simultaneously senses second light data used in determining of a second of the at least two patient parameters.

In another embodiment, a method for simultaneously monitoring at least two patient parameters is provided. The method includes the activities of pressurizing a respective cuff of a cuff pair positioned on adjacent digits of a patient, each cuff of the cuff pair including a light emitting device and sensor that can sense light data for use in determining at least two patient parameters. First light data used in determining a first patient parameter is sensed using the sensor in the respective pressurized cuff and data representing the first patient parameter based on the first light data is determined. Second light data used in determining a second patient parameter is simultaneously sensed using the sensor in the other of the respective cuff, the other of the respective cuff being unpressurized and data representing the second patient parameter based on the second light data is determined. Data representing the first and second patient parameter is output for use by a healthcare professional charged with monitoring the patient.

In a further embodiment, an apparatus is provided that measures at least two patient parameters. The apparatus includes a first cuff including a first inflatable bladder, a first light emitting device emitting a first and second type of light and a first sensor that senses first and second light data for use in calculating at least two patient parameters. A controller coupled the sensor, and when the controller causes the bladder of the first cuff to inflate, the first sensor senses first light data used in determining a first of the at least two patient parameters and simultaneously senses second light data used in determining of a second of the at least two patient parameters.

These and other features and advantages of the present invention will become more readily appreciated from the detailed description of the invention that follows.

BRIEF DESCRIPTION OF THE DRAWINGS

The following figures depict certain illustrative embodiments of the invention in which like reference numerals refer to like elements. These depicted embodiments are to be understood as illustrative of the invention and not as limiting in any way.

DETAILED DESCRIPTION OF THE INVENTION

Figure 1:
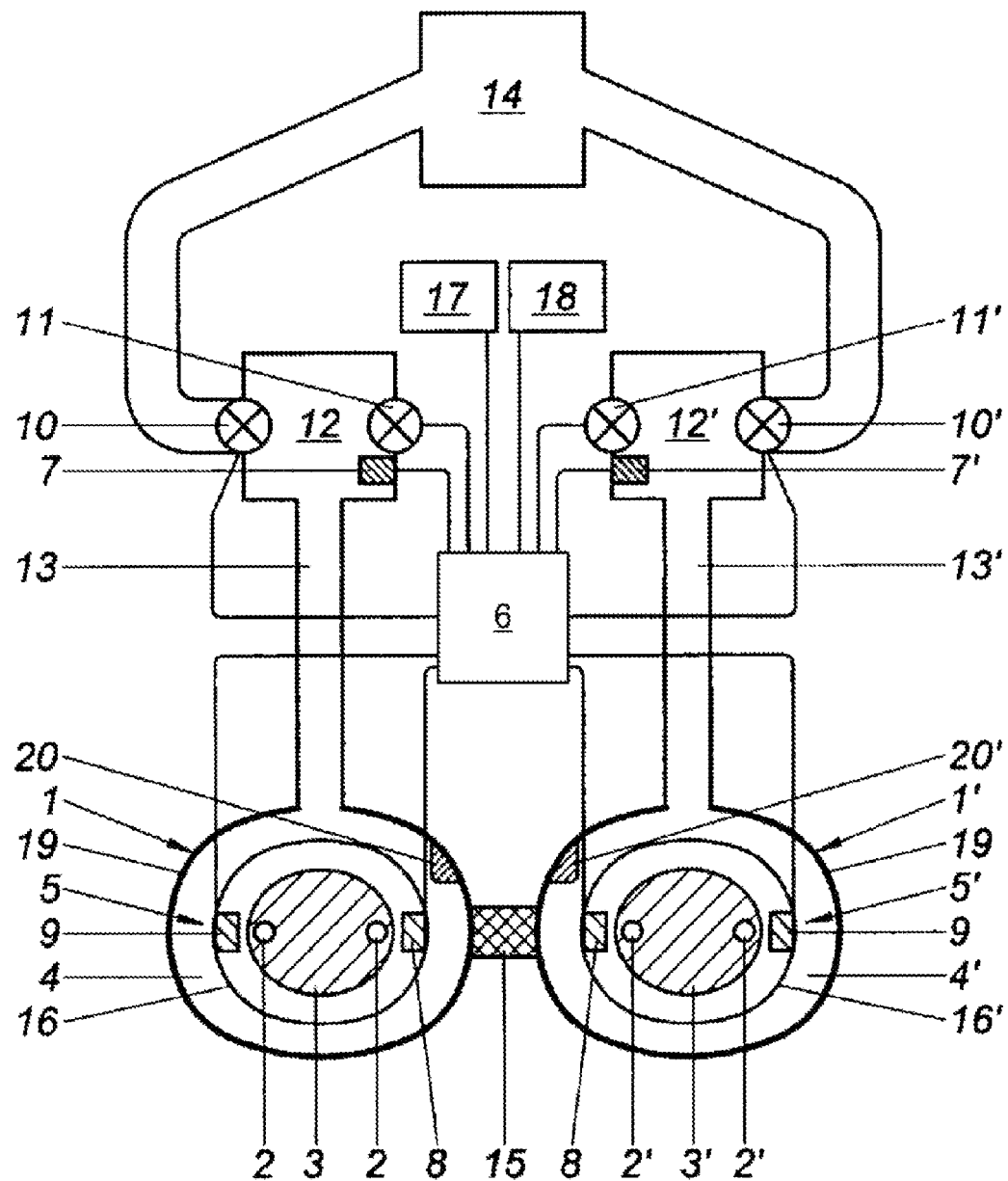
FIG. 1 is a schematic diagrammatic view of a device for simultaneous continuous, non-invasive arterial blood pressure (CNAP) and SpO2 measurements according to invention principles.

The combined CNAP and pulse oximetry (hereinafter, "dual sensor") apparatus advantageously utilizes a dual finger cuff which alternates blood pressure measurements between respective finger cuffs. When one finger cuff measures SpO2 data the other finger cuff measures CNAP data and vice versa. By combining the measurement of two common medical parameters into a single device, the apparatus advantageously reduces clutter and improves cable management in and around a patient. Moreover, the apparatus enables measurement of key medical parameters while reducing the number of physical sensors connected to the patient. By reducing the number of physical sensors connected to the patient, the apparatus advantageously reduces any instances of erroneous parameter measurement due to a sensor being dislodged from the patient. Reducing the number of physical sensors connected to the patient provides the further advantage of improving patient comfort and mobility while being monitored. The apparatus may also advantageously monitor SpO2 data in both finger cuffs simultaneously. Thus, the cuff measuring CNAP data also measures SpO2 data at the same time while the other cuff only measures SpO2 data. The simultaneous measurement of SpO2 data using both sensors advantageously provides a mechanism for comparison that may be used to identify a medical condition of a patient. Additionally, the simultaneous measurement of CNAP and SpO2 in a single cuff advantageously provides a feedback control mechanism to monitor the effectiveness of the CNAP measurement and modify the CNAP measurement procedure in response to particular SpO2 measurements thereby improving patient comfort and reducing the risk of prolonged venous congestion. The finger cuff may also employ an adjustable cuff selectively securable by hook and loop fasteners, similar to conventional blood pressure cuffs utilized on neonates, which provides a superior patient-specific fit as compared to the conventional rigid cuff enclosure typically employed in stand-alone CNAP and/or SpO2 sensors. The adjustable dual sensor apparatus cuff provides for a cuff design adaptable to the patient's finger circumference and will make the cuff optionally either a single-use or a reusable cuff. Single-use or single patient-use accessories are advantageous in the medical field because they can reduce cross-contamination between patients or between patients and healthcare providers. They are also cost-effective and can reduce the end price of the device and ultimately the cost of the monitoring procedure.

The dual sensor includes two substantially identical pressure cuffs with an inflatable bladder positioned preferably over adjacent fingers. Each of the pressure cuffs also includes a sensor that is able to monitor at least two patient parameters. In one embodiment, the patient parameters may include CNAP data and SpO2 data. The sensor may be a blood volume sensitive sensor, i.e., a SpO2 sensor, capable of measuring blood volume as well as blood oxygen saturation. The sensor may include two light sources, typically one LED emitting light in the red wavelength range and one infrared LED (IR-LED). The sensor may employ both light sources when measuring SpO2 data and one light source (e.g. the LED emitting light in the red wavelength) when measuring CNAP data. The CNAP and SpO2 sensors also include one or more photodetectors, arranged substantially on an opposite side of the cuff relative to the light sources. The same red LED and associated photodetector may be used for both CNAP and SpO2 measurements. The redundancy of sensors greatly reduces the incidence of false warnings and minimizes the cost in producing the apparatus. Redundant sensors also reduce the cost to healthcare enterprises when monitoring patients as well as reducing costs to insurance companies who cover patient costs for patient monitoring during an in-patient stay.

The two finger cuffs may be inflated and pressed into service in regular time intervals alternating between CNAP and SpO2 measurements so that the blood flow in the patient's finger is not constricted for a time period that would cause undue discomfort or tissue damage. Additionally, SpO2 measurements may also be taken on the cuff that is inflated as well as the cuff that is not inflated. Thus, the SpO2 measurement in the inflated cuff may be used to control the inflation in that cuff. This measurement may also be used to control and modify the CNAP algorithm to prevent patient discomfort by automatically alternating between which cuff is inflated. Incorporating into the finger cuff design an SpO2 sensor that uses conventional pulse oximetry technology to provide oxygen saturation values in addition to continuous, non-invasive blood pressure eliminates the need for using an additional digit and hence reduces the number of accessories attached to the patient and improves cable management.

In a method for continuous, non-invasive measurement of blood pressure (CNAP) and blood oxygen saturation level (SpO2), pressure cuffs which can be controllably and separately inflated are placed over two or more fingers, pressure in a first pressure measuring chamber connected to a first of the pressure cuffs is controlled depending on a measurement signal of a plethysmographic sensor device in such a way that a difference between an amplitude of the plethysmographic measurement signal and a predetermined value is minimized, which then provides a blood pressure reading. During the time of the blood pressure measurement in a first cuff, the blood oxygen saturation level is measured with another cuff on another finger not currently used for the blood pressure reading. Because the pressure cuffs include optical emitters and sensors for both blood pressure measurements and SpO2 measurements, the role of the cuffs and their operation can be interchanged, so that in a subsequent measurement, the first cuff is used to measure the blood oxygen saturation level, while the other cuff or cuffs are used to obtain a blood pressure reading.

The device may operate by inflating a first cuff for CNAP measurements, while the SpO2 signal is acquired with the second cuff on the other finger (not inflated). Optionally, a reference pressure measurement is performed first, before the actual blood pressure is measured. CNAP/SpO2 measurements typically have a duration of about 15 minutes, after which time the operation of the cuffs is reversed, i.e. the second cuff is inflated and CNAP measurements are taken with the second cuff, while the first cuff is deflated and used for SpO2 measurements. In this way, both CNAP and SpO2 measurements can be taken with a simple device having two substantially identical cuffs which are preferably interconnected and applied on adjacent fingers.

Devices and methods are described that allow simultaneous continuous, non-invasive arterial blood pressure (CNAP) and SpO2 measurements on two or more, preferably adjacent, fingers.

FIG. 1 shows an exemplary embodiment of the dual sensor apparatus that is able to simultaneously sense at least two patient parameters from a patient to which the apparatus is connected. In one embodiment the at least two patient parameters include any combination of (a) arterial blood pressure; (b) SpO2; and (c) temperature at the surface of the skin. The dual sensor apparatus enables the at least two patient parameters to be measured continuously and in a non-invasive manner. The dual sensor apparatus includes a first pressure cuff 1 having an inner wall 16 and an outer wall 19, which can releasably receive a first body part or body region 3, such as a finger, containing an artery 2. A first inflatable pressure measuring chamber 4 is positioned between the inner wall 16 and the outer wall 19. The cuff 1 further includes a first plethysmographic sensor device 5 positioned on the inner wall 16 adjacent the position of a body part or region 3 when inserted into the cuff. The apparatus further includes a second pressure cuff 1' having an inner wall 16' and an outer wall 19', which can releasably receive a second body part or body region 3' containing an artery 2', such as a finger adjacent the finger received by the first cuff 1. A second inflatable pressure measuring chamber 4' of the same design as the pressure measuring chamber 4 is positioned between the inner wall 16' and outer wall 19'. The second pressure cuff 1' includes a second plethysmographic sensor unit 5' positioned on the inner wall 16' adjacent the position of a body part or region 3' when inserted into the cuff 1'. The pressure measuring chambers 4, 4' are each connected with a corresponding pressure sensor 7, 7' to obtain a pressure measurement signal derived by sensing the pressure in the measuring chambers 4, 4'.

The plethysmographic sensor devices 5, 5' each include light emitters 8 and light detectors 9 and are thus able to detect the pulsating changes of the irradiated volume of blood within arteries 2 included in the intra-arterial blood pressure determination therein as well as an oxygenation level of the blood of the patient. In one embodiment, the light emitters 8 in each of plethysmographic sensors 5, 5' are able to emit a first type of light having a first wavelength and a second type of light that includes successive emission of light in the first wavelength followed by emission of light in a second different wavelength. For example, the emitter 8 may include an LED that emits light in (a) a red wavelength and (b) an infra-red (IR) wavelength. In another embodiment, the emitter may include two discrete LEDs each emitting a particular type of light in a particular spectrum such that one LED emits the light at the first wavelength and the second LED emits light at two different wavelengths (the first wavelength and second wavelength). Additionally, the particular type of light emitted by emitter 8 is described for purposes of example only and the apparatus may employ an emitter 8 that emits any type of light in any wavelength depending on the type of patient parameter to be measured. The emitter 8 may emit a single type of light at any given time or, alternatively two different types of light at a given time. One skilled in the art will recognize that two or more emitters that produce light of wavelengths other than red and infrared may be utilized in either of the embodiments to perform measurements of oxygen saturation other than SpO2 (e.g., hemoglobin (SpHb), oxygen content (SpOC), carboxyhemoglobin (SpCO), or methemoglobin (SpMet)).

The pressure measuring chambers 4, 4' are connected via pressure lines 13, 13' to pressure control chambers 12, 12'. Inlet valves 10, 10' and outlet valves 11, 11' of the pressure measuring chambers 4, 4' may be placed, as illustrated, in the separate pressure control chambers 12, 12'. The inlet valves 10, 10' selectively connect a pressure source 14 with the pressure control chambers 12, 12'. The outlet valves 11, 11' selectively connect the pressure control chambers 12, 12' with the pressure lines 13, 13'. Alternatively, the outlet valves 11, 11' may be positioned between the pressure lines 13, 13' and the pressure measuring chambers 4, 4'. Pressure is provided from the pressure source 14, through inlet valves 10, 10' and received in the pressure control chambers 12, 12'. At predetermined intervals, the outlet valves 11, 11' are selectively opened allowing pressure to flow through the pressure lines 13, 13' and into the pressure measuring chambers 4, 4' thereby pressurizing the cuff 1, 1'. Alternatively, the pressure measuring chambers 4, 4' may be combined into a single chamber (not shown).

In one embodiment, the two pressure cuffs 1, 1' may be connected by a connecting element 15, forming a double finger cuff. The pressure chambers 4, 4' are each provided on the inside with an easily distensible inner wall membrane 16, 16'. Prior to measurement, the two pressure chambers 4, 4' of the double finger cuff are slipped onto adjacent fingers 3, 3', whereby the light emitters 8 and light detectors 9 are automatically positioned adjacent at least one blood vessel. The valves 10, 11 and 10', 11' of the pressure control chambers 12, 12' are controlled, for example, by a controller 6. The pressure cuffs 1, 1' may be formed from a non-rigid material that allows for the diameter of the cuff 1, 1' to be selectively modified by a user when affixing the cuff 1, 1' to the patient. The non-rigid, selectively modifiable diameter of the cuffs 1, 1' advantageously enable a patient specific fit of the cuff 1, 1' each time the cuffs 1, 1' are connected to the user. Further, the non-rigid material from which the cuffs 1, 1' are made enables the sensors 5, 5' to be positioned more precisely with respect to the arteries in the body part to which the cuffs 1, 1' are connected. This advantageously provides more precise parameter measurements while minimizing monitoring errors resulting from an imprecise fit of the rigid cuffs that are conventionally used to monitor patient parameter data. An example of non-rigid cuffs 1, 1' is shown in FIG. 2 and will be discussed in greater detail with respect thereto.

A controller 6 is selectively connected to pressurize the pressure measuring chambers 4, 4' and may be used to run different control tasks, for example, alternatingly using the pressure source 14 to inflate one of the pressure measuring chambers 4, 4'. The controller 6 may also control the light emitters 8 and the light detectors 9 for CNAP as well as SpO2 measurements. The controller 6 may also control a display unit 17 and an alarm unit 18. A temperature sensor 20, 20' may also be placed in or on the chamber walls of each cuff 1, 1'. The operation of the controller 6 and the tasks controlled thereby will be discussed below with respect to FIG. 3.

Figure 2:
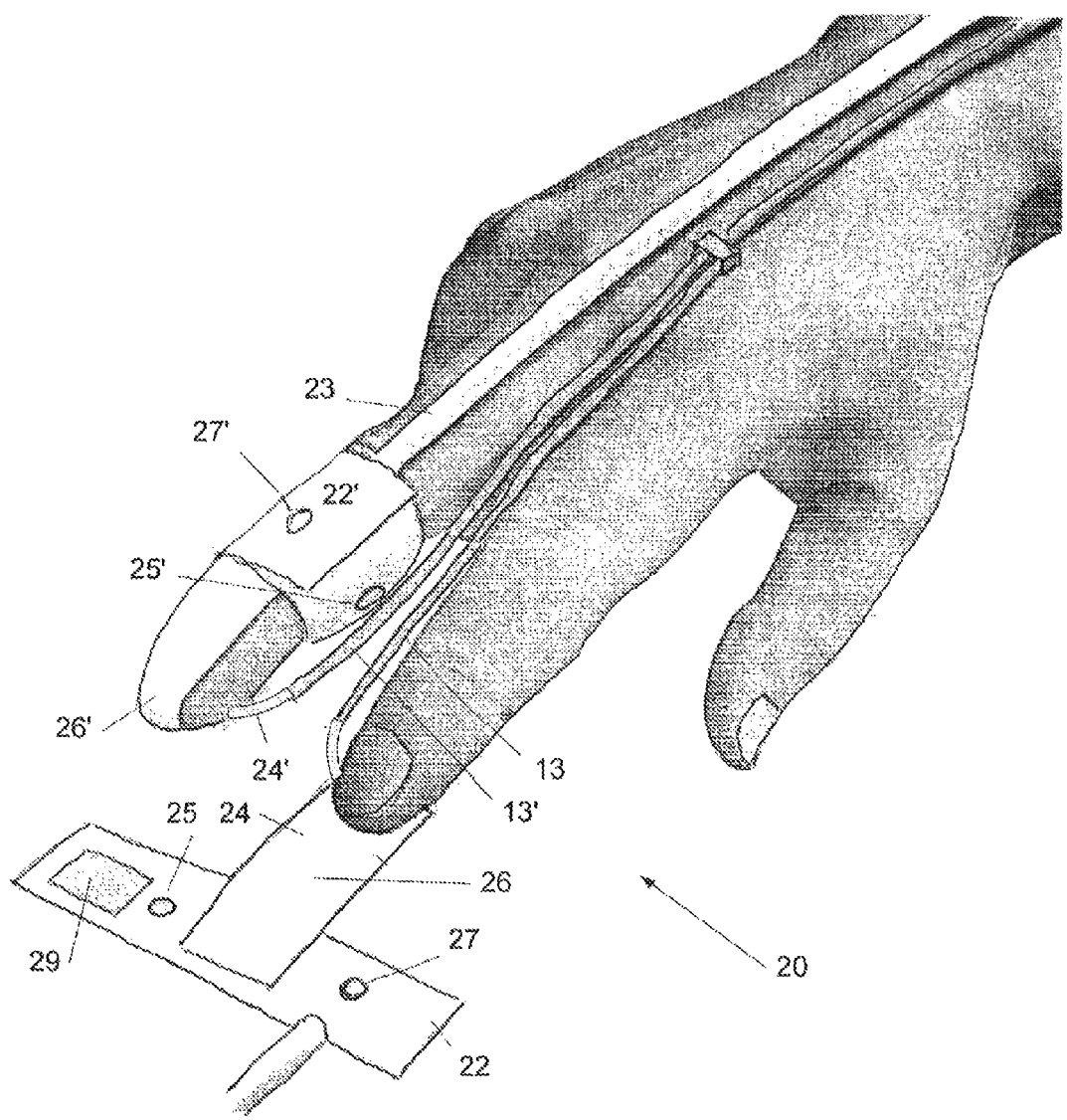
FIG. 2 is a perspective view of an adjustable cuff incorporating LEDs and optical sensors for simultaneous continuous, non-invasive arterial blood pressure (CNAP) and SpO2 measurements according to invention principles.

Turning now to FIG. 2, which illustrates the cuffs 1, 1' of FIG. 1 as being adjustable and labeled with reference numeral 20. The adjustable finger cuff 20 includes a first pressure cuff 22 with an inflatable bladder 24 and a second pressure cuff 22' with inflatable bladder 24' positioned over adjacent fingers. The inflatable bladders 24, 24' correspond to the pressure measurement chambers in FIG. 1. The cuff 20 further includes SpO2/blood volume sensors 26, 26' and cuff controller cables 23, 23' that connect the pressure cuffs 22, 22' to a CNAP/SpO2 measuring device (not shown in FIG. 2). Each sensor 26, 26' is capable of measuring blood volume as well as blood oxygen saturation. As mentioned above, a typical sensor 26, 26' includes two light sources (red and IR). However, those skilled in the art will understand that additional light sources may be included in a SpO2/blood volume sensor.

The blood volume sensitive (plethysmographic) sensors 26, 26' for the measurement of blood oxygen saturation may be positioned distal to the pressure measuring cuffs 22, 22' (a first embodiment shown on the index finger in FIG. 2) or may be affixed to the pressure cuffs (a second embodiment shown on the middle finger in FIG. 2). In the first embodiment, the short edge of the sensor 26, 26' that is fixed opposite the nail bed is affixed perpendicular to the pressure cuff by an adhesive mechanism 29 such as hook and loop fasteners.

In the first embodiment, conventional pulse oximetry is used and a light emitter 25, 25' with red and infrared LEDs and a corresponding photodetector 27, 27' are incorporated into the sensors 26, 26'. The first embodiment uses both IR and red light sources, with the sensors 26, 26' being placed distal to the cuff 22, 22'. While the pressure cuff 22, 22' is inflated, the IR light source 25 incorporated in the sensor 26, 26' is used to acquire measurements of blood volume. Current CNAP technology utilizes an infrared light source in the pressure cuff to measure blood volume and to control cuff pressure to maintain a constant blood volume. As cuff 22 is inflated, the IR light source is used to measure CNAP data in cuff 22. Simultaneously, cuff 22' is not inflated and the IR and red light sources 25' incorporated in the sensor 26' of cuff 22' are used to acquire measurements of oxygen saturation (SpO2). Conversely, when cuff 22' is inflated, sensor 26 in cuff 22 is used to measure SpO2.

In the second embodiment, the light emitter 25, 25' and photodetector 27, 27' are incorporated into the cuff bladder 24, 24'. The pressure measuring cuffs 22, 22' are each equipped with a light emitter 25, 25' that incorporates both red and IR light sources and a corresponding light detector 27, 27' that are incorporated at locations selected to increase the likelihood of placement over arteries in the finger. The IR LEDs incorporated into the emitters are the same as those already employed in pulse oximetry. Therefore, this embodiment includes both red and IR light sources utilized in conventional pulse oximetry, i.e., the IR LEDs are used for both oximetry and CNAP measurements. Similar to the first embodiment, while cuff 22 is inflated, the infrared light source 25 and sensor 27 in cuff 22 is used to acquire measurements of blood volume and the sensor 27' incorporated in cuff 22' is used to acquire measurements of oxygen saturation. The exemplary device of the invention using the hook and loop fastener for adjusting the size of the finger cuff prevents the cuff from sliding upward over the phalangeal joints, thereby reducing measurement errors.

With the above design, it would be beneficial to first complete sensor attachment before the position of a pressure cuff 22, 22' is adjusted around the finger, thus avoiding the phalangeal joints. In this way, the light emitter 25, 25' and light detector 27, 27' in the pressure cuff are optimally positioned over the respective finger.

In one exemplary embodiment, the device may incorporate separate cuff controller cables 13, 13' and 23, 23' (see also FIG. 1) for connecting electrical 27 and pressure 28 lines between the controller 6 (FIG. 1) and the pressure cuffs 22, 22' with the light emitters 25, 25' and light detectors 27, 27'. In another exemplary embodiment (not illustrated), cables 13, 13' and 23, 23' may be replaced by a single cable that may extend from the controller and eventually split into two separate cables that connect to each pressure cuff 22, 22'. A rigid cable facilitates handling and operation by ensuring that the pneumatic feeds to the cuff are constant and unobstructed.

Additionally, the apparatus may include a plurality of fittings and connectors to allow the finger cuff and sensor to be disconnected from the cuff controller cable. This will facilitate the use of disposable cuffs. Additionally, the cuff controller cable may be disconnected from the CNAP/SpO2 measuring device.

Figure 3:
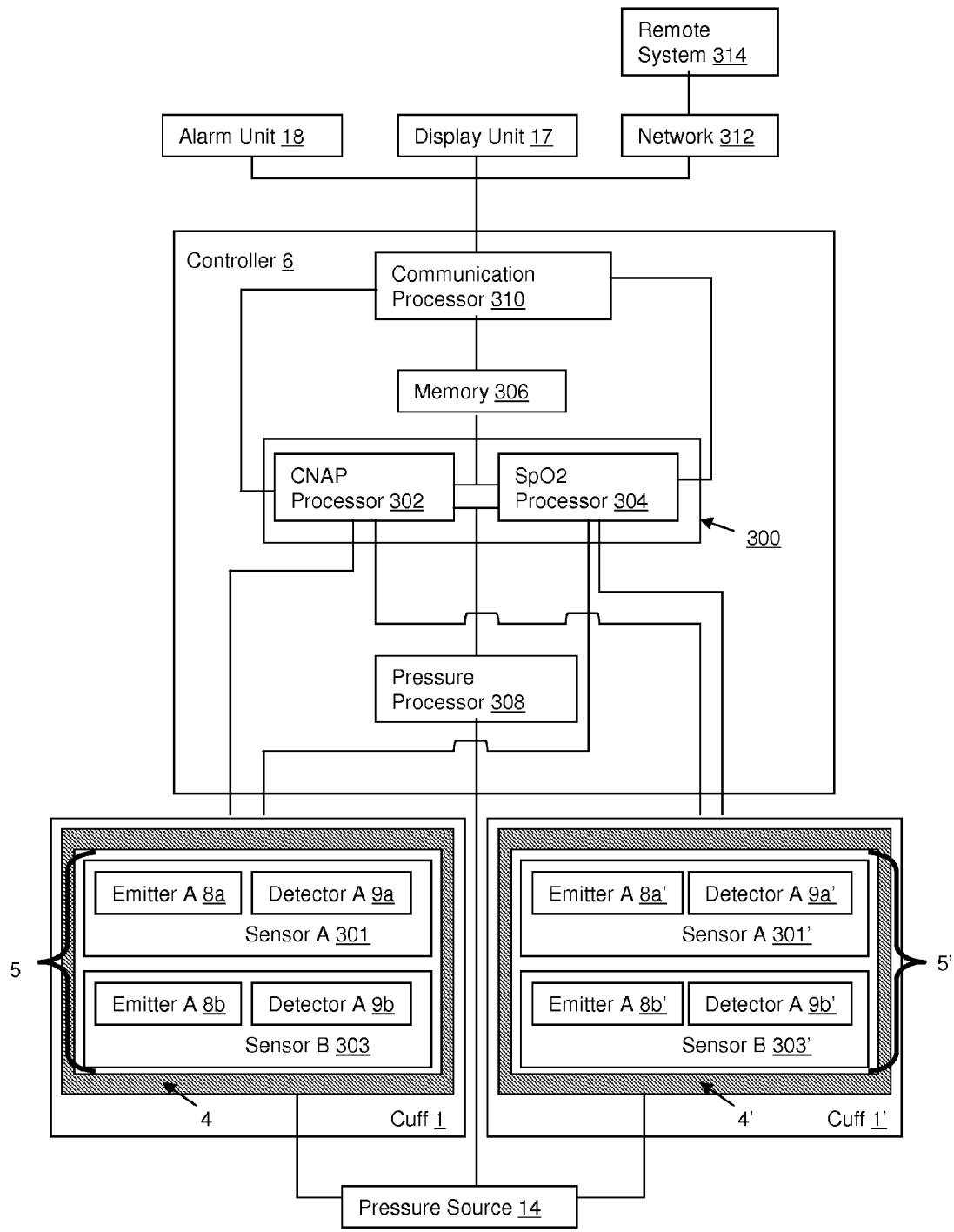
FIG. 3 is an exemplary block diagram of the apparatus according to invention principles.

FIG. 3 is an exemplary block diagram of the dual sensor apparatus further describing the elements of the controller 6 shown in FIG. 1. As discussed above with respect to FIG. 1, the controller 6 is selectively connected to the first cuff 1 and the second cuff 1' in order to selectively monitor at least two patient parameters simultaneously. The cuffs 1, 1' include the pressure measurement chambers 4, 4' which are connected to and may be selectively pressurized by the pressure source 14 in response to a control signal generated by the controller 6 as discussed below. The cuffs 1, 1' further include the sensor units 5, 5' that may include sensors for sensing at least two patient parameters using plethysmographic sensors. The sensor units 5, 5' may include first sensors 301, 301' that sense a first patient parameter and second sensors 303, 303' that sense a second patient parameter. First sensors 301, 301' include light emitters $8a$, $8a'$ that emit a first type of light and corresponding detectors $9a$, $9a'$ that are able to selectively detect a density of the first type of light passing through the part of the body to which the cuff 1, 1' is connected. Second sensors 303, 303' may include light emitters $8b$, $8b'$ that emit a second type of light and corresponding detectors $9b$, $9b'$ that are able to selectively detect a density of the second type of light as the second type of light passes through the part of the body to which the cuff 1, 1' is connected. The first type of light may be light within a first range of wavelengths and the second type of light may include light having two different wavelength, one wavelength being the within the first rage of wavelengths and a second being within a second range of wavelengths. In one embodiment, the emitters $8a$, $8a'$ are LED emitters that emit light in the red wavelength (~700 nm-635 nm) range and the emitters $8b$, $8b'$ are LED emitters that emit light in both the red and the infrared wavelengths (>1000 nm). The sensor units 5, 5' including two sensors 301, 303 and 301', 303' is described for purposes of example only and one skilled in the art will understand that a single sensor that is able to emit light at two different wavelength simultaneously coupled with a detector able to detect two different wavelengths simultaneously may be employed.

The controller 6 selectively controls the pressure within the pressure measuring chamber 4, 4' as well as the operation of the sensor units 5, 5'. The controller 6 may include a parameter processor 300 that selectively controls the monitoring of at least two patient parameters. The parameter processor 300 may include a CNAP processor 302 that selectively controls the sensor units 5, 5' to sense an arterial pressure within the part of the body to which one of the respective cuffs 1, 1' is attached. The manner in which arterial pressure is measured by the apparatus may employ the vascular unloading technique and is well known in the art. The parameter processor 300 may also include an SpO2 processor 304 that selectively controls the sensor units 5, 5' to sense data representing a blood oxygen saturation level of the patient. The SpO2 processor 304 employs pulse oximetry techniques that are known in the art in order to derive the blood oxygen saturation level of the patient by sequentially passing light at the first wavelength and light at the second wavelength through the part of the body to which the cuff 1, 1' is connected. By sequentially passing two different wavelengths of light through the body, the detector 9b, 9b' is able to determine the ratio of changing absorbance of the two different wavelengths of light caused by the difference in color of oxygenated versus deoxygenated hemoglobin in the blood. The description of the parameter processor 300 including both the CNAP processor 302 and SpO2 processor 304 as being separate processors is described for purposes of example only and to clearly espouse the operation and function of each. One skilled in the art would understand that the arterial pressure monitoring and blood oxygen saturation monitoring maybe performed by a single processing device. For purposes of ease of understanding, the discussion of the parameter processor 300 should be understood as including any one of the CNAP processor 302 and SpO2 processor 304, or the combination thereof unless specified otherwise.

The parameter processor 300 is shown being directly connected to the cuffs 1, 1' for purposes of simplicity and clarity. However, one skilled in the art will appreciate that the CNAP processor 302 and the SpO2 processor 304 may each be connected directly to the sensor units 5, 5' and, more specifically, may be connected directly to first sensors 301, 301' and/or second sensors 303, 303' enabling direct control over the particular sensors that make up the sensor units 5, 5'. Thus, the parameter processor 300 may selectively receive and process data sensed by the sensor units 5, 5' in order to derive arterial pressure data and blood oxygen saturation data therefrom. Alternatively, in order to minimize circuit complexity, the controller 6 may employ a multiplexer to connect the patient parameter processor 300 to the sensor units 5, 5' in cuffs 1, 1'.

A memory 306 may be connected to the parameter processor 300. The memory 306 includes a data storage medium able to store at least one of analog or digital data therein. The CNAP processor 302 and the SpO2 processor 304 selectively cause data derived from respective sensor units 5, 5' including arterial pressure data and blood oxygen saturation data to be stored in the memory 306 at predetermined time intervals for predetermined durations. The CNAP processor 302 and SpO2 processor 304 may selectively query data stored in memory 306 at predetermined intervals in order to determine if the respective parameter monitoring algorithm employed by the CNAP processor 302 or SpO2 processor 304 should be modified in any manner as will be discussed below.

A communication processor 310 may also be selectively coupled to the parameter processor 300. The parameter processor 300 may generate control signals that control the communication processor 310 to selectively communicate data to at least one of a display unit 17, an alarm unit 18 and to a remote computing system 314 via a communications network 312. The data communicated by the communication processor 310 may include any data sensed or derived by the parameter processor 300 including arterial blood pressure data and blood oxygen saturation data. In one embodiment, arterial blood pressure data and blood oxygen saturation data may be selectively communicated at least one of (a) simultaneously; (b) sequentially; (c) in response to the parameter processor 300 determining that a type of data has reached, exceeded, or fallen below a threshold value; and (d) in response to receipt of an external request (user generated or automatically generated by a computing system) requesting a particular type of data be transmitted. In another embodiment, the parameter processor 300 may generate a control signal causing the communication processor 310 to query and communicate data stored in memory 306. In this embodiment, the communication processor 310 may cause a set of data sensed by sensor units 5, 5' and that is stored in memory 306 to be selectively communicated via network 312 to a remote computing system 314 (e.g. hospital information system) to automatically update a patient record with arterial blood pressure data and blood oxygen saturation data at a particular time interval. The communication processor 310 may also be able to selectively receive control requests from remote computing systems 314 (or users thereof) that selectively modify the operation of the apparatus. In a further embodiment, the patient parameter processor 300 may automatically and in real-time compare patient parameter data to threshold parameter values and, if the sensed patient parameter data at least one of (a) equals a threshold; (b) exceeds a threshold; and (c) falls below a threshold, the patient parameter processor 300 may selectively control the communication processor 310 to signal at least one of the display unit 17 or alarm unit 18 to notify a healthcare professional that the patient may be in trouble and require assistance.

The controller 6 may also include a pressure processor 308 that may be connected to the parameter processor 300. The pressure processor 308 may selectively monitor the pressure in the pressure measuring chambers 4, 4' of cuffs 1, 1' in order to obtain at least one of arterial pressure data and blood oxygen saturation data. The pressure processor 308 may also be selectively connected to the pressure source 14 for controlling an amount of pressure that is provided to respective pressure measurement chambers 4, 4'. The pressure processor 308 is shown for purposes of example only and one skilled in the art would understand that the parameter processor 300 may selectively perform any and all functions performed by the pressure processor 308 including measuring a pressure level in respective cuffs 1, 1' and controlling the pressurization of the cuffs 1, 1' via the pressure source 14.

In a first mode of operation, the CNAP processor 302 signals the pressure processor 308 to pressurize the pressure measurement chamber 4 in cuff 1 in order to obtain arterial pressure data from the finger on which cuff 1 is positioned. The CNAP processor 302 automatically causes the first emitter 8a in cuff 1 to emit the first type of light (red wavelength). The first type of light passes at least partially through the finger and arteries contained therein and a remaining amount of the first type of light is detected by detector 9a. The amount of the first type of light detected by detector 9a is provided to the CNAP processor 302 in order to (a) based on the pulsatile nature of arterial blood flow, selectively control the pressure processor 308 to modify a pressure level in the pressure measurement chamber 4 until a pressure level in the chamber 4 is equal to the mean pressure level in the arteries of the finger and (b) calculate the arterial pressure value based on the sensed amount of first type of light detected by detector 9a and the corresponding pneumatic pressure within cuff 1. The CNAP processor 302 selectively monitors arterial pressure data in this manner over a predetermined time period (e.g. between 30 and 60 minutes).

Also during the first mode of operation, cuff 1' is not pressurized and the SpO2 processor 304 causes the at least one of emitter 8b' of the sensor unit 303' to emit the second type of light that includes a sequential emission of a pulse of light at the first wavelength and a pulse of light at the second wavelength. The second type of light passes through the finger on which cuff 1' is positioned. The detector 9b' is able to selectively detect an amount of the second type of light that passes through the finger in cuff 1'. Values corresponding to an absorbance of the first wavelength of light and the second wavelength of light passing through the finger are provided to the SpO2 processor 304 to selectively determine blood oxygen saturation level for the patient in a known manner.

At the expiration of the predetermined time period, the CNAP processor 302 causes the pressure processor 308 and pressure source 14 to depressurize the chamber 4 in cuff 1 and automatically pressurize the pressure measurement chamber 4' in the second cuff 1' and use the second cuff 1' to determine arterial pressure data for the patient. Upon determining that the second cuff 1' is being pressurized, the SpO2 processor 304 automatically uses the emitter 8b and detector 9b to derive blood oxygen saturation data. Thus, in the first mode of operation, the type of parameter being monitored by a respective cuff alternates between arterial pressure monitoring and blood oxygen saturation monitoring and each cuff 1, 1' is charged with measuring a single patient parameter. Generally, the operation of the first mode is time based and cuff pressurization alternates at fixed intervals. However, any of the CNAP processor 302 or SpO2 processor 304 may selectively and continually monitor data sensed by the sensing units and automatically switch which of cuff 1 or 1' is being pressurized at a given time in response to at least one of arterial pressure data and blood oxygen saturation data.

Also in the first mode of operation, the data derived by the CNAP processor 302 and the SpO2 processor 304 may be selectively stored in memory 306 and communicated by communication processor 310 to the remote computing system 314 via the communication network 312. The communication processor 310 may also receive a signal causing the predetermined time period to end prematurely in response to at least one of the arterial pressure data, blood oxygen saturation data or a combination thereof.

The controller 6 may operate in a second mode as well. The second mode of operation is similar to the first mode of operation with one difference. In the second mode of operation, the cuff 1, 1' that is pressurized measures both arterial pressure data and blood oxygen saturation data. Exemplary operation in the second mode will be discussed with respect to cuff 1 being pressurized as described above. In addition to the CNAP processor 302 causing emitter 8a to emit the first type of light which is detected by detector 9a, the SpO2 processor 304 causes emitter 8b to emit the second type of light which is detected by detector 9b. A value corresponding to arterial blood pressure is derived by the CNAP processor 302 in response to the absorbance of the first type of light detected by detector 9a and a value corresponding to blood oxygen saturation level is derived by the SpO2 processor 304 in response to the absorbance of the second type of light detected by detector 9b.

Alternatively, in an embodiment where a single light emitter and detector is present, the light emitter is able to selectively and sequentially emit light at first wavelength (e.g. red) and a second wavelength (e.g. IR). In this embodiment, the absorbance of the light of a first wavelength as detected by the detector is used by both the CNAP processor 302 to calculate arterial pressure data and the SpO2 processor 304 as part of the calculation of blood oxygen saturation level. In the embodiment with the single light emitter, once the absorbance of light having the first wavelength is detected, the emitter emits the light having the second wavelength and the absorbance of the light having the second wavelength is detected by the detector and provided to the SpO2 processor 304 to be combined with absorbance of the first wavelength of light in order to complete the calculation of blood oxygen saturation data in the known manner.

In another embodiment, blood oxygen saturation data is used to selectively control and/or modify the operation of the CNAP processor 302 and the algorithm employed thereby to monitor arterial pressure. In this embodiment, blood oxygen saturation data may be derived from either the pressurized cuff or the unpressurized cuff. For example, the venous blood oxygen saturation level within the finger being pressurized by cuff 1 may fall below a threshold level indicating that pressurization has occurred for too long and may be causing the patient discomfort. This determination may be made because red light absorption increases as the hemoglobin in the blood becomes more deoxygenated causing an amount of red light detected by the detector 9 to decrease. The decrease in an amount of red light detected by the detector 9 may be indicative of venous congestion in the finger being pressurized by cuff 1 and therefore may indicate that the pressure being applied thereto is either too great in magnitude or too prolonged thus causing the CNAP processor 302 to signal the pressure processor 308 to at least one of (a) automatically modify the pressure of the pressurized chamber 4 and (b) depressurize the chamber 4 and pressurize chamber 4' in the second cuff 1'.

Furthermore, in the second mode of operation, two values corresponding to blood oxygen saturation level are determined by the SpO2 processor 304. One is derived from the pressurize cuff and is used to selectively control the operation of the CNAP processor 302 and the second, which is derived from the non-pressurized cuff is determined as discussed above in the first mode of operation.

Figure 4A:
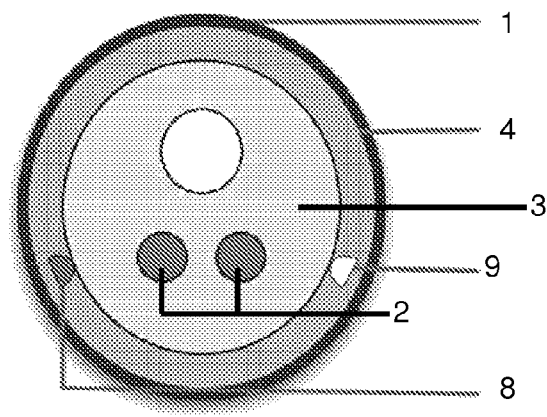
FIGS. 4A-4C are illustrative views of a finger having the apparatus according to invention principles positioned thereon.
Figure 4B:
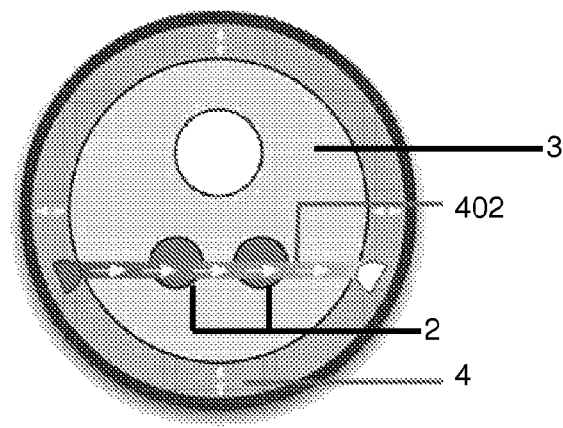
Figure 4C:
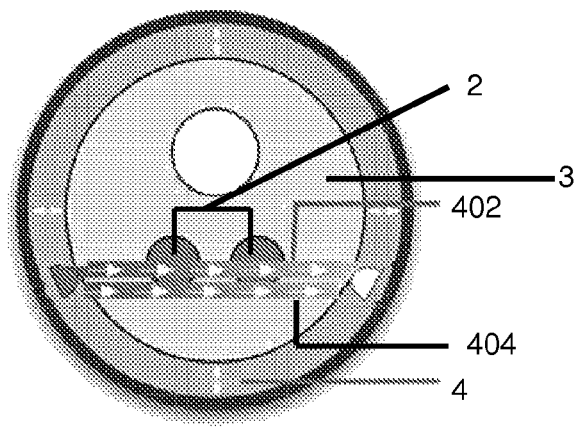

FIGS. 4A-4C are visual depictions of how the first and second parameter data are derived by the apparatus. FIG. 4A is a cross section of a finger 3 having cuff 1 positioned thereon. The cuff 1 includes the emitter 8 and detector 9 positioned substantially adjacent the arteries 2 in the finger 3. Although not shown, the second cuff 1' includes similar elements arranged in a similar manner.

FIG. 4B is a visual depiction of the first cuff 1 (pressurized) in the first mode of operation described above in FIG. 3. In this Figure, emitter 8 is emitting the first type of light 402 which passes through the finger 3 and arteries 2 and is detected by detector 9. In this mode of operation, the controller 6 is controlling a pressure in the pressure measurement chamber 4 in order to derive arterial pressure data for the patient. The arrows shown within chamber 4 indicate that the pressure level therein may change in response to controller operation. While FIG. 4B shows the first mode of operation in the first cuff 1, one skilled in the art will appreciate that the blood oxygen saturation level of the second cuff 1' is determined in a similar manner with the exception that the emitter emits the second type of light and the pressure measurement chamber 4' in cuff 1' remains unpressurized.

FIG. 4C is a visual depiction of the first cuff 1 (pressurized) in the second mode of operation. In this second mode of operation, the emitter 8 is emitting the second type of light which includes the light having a first wavelength 402 (e.g. Red) that is used in deriving arterial pressure data and as part of the calculation in determining blood oxygen saturation data. The emitter 8 also emits light having a second wavelength 404 (e.g. IR) that, when combined with the first wavelength light 402 may be used to derive blood oxygen saturation data. The detector 9 is able to selectively detect the first and second wavelengths of light and discriminate therebetween in order to provide data representing the absorption of light having the first wavelength and data representing the absorption of the light having the second wavelength that passes through the arteries 2 of finger 3. In this mode of operation, the controller 6 is controlling a pressure in the pressure measurement chamber 4 in order to derive arterial pressure data for the patient while simultaneously sensing a blood oxygen saturation level in the same finger 3. The arrows shown within chamber 4 indicate that the pressure level therein may change in response to controller operation. While FIG. 4C shows the second mode of operation in the first pressurized cuff 1, one skilled in the art will appreciate that the blood oxygen saturation level of the second cuff 1' is determined in a similar manner with the exception that emitter emits only the second type of light and the pressure measurement chamber 4' in cuff 1' remains unpressurized.

Figure 5A:
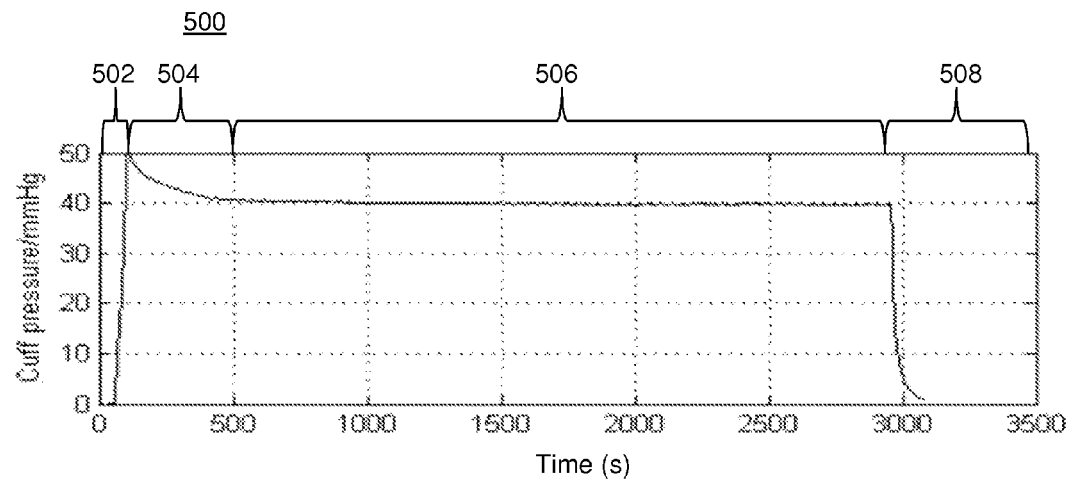
FIGS. 5A-5B are graphical depictions of data sensed by the apparatus according to invention principles.
Figure 5B:
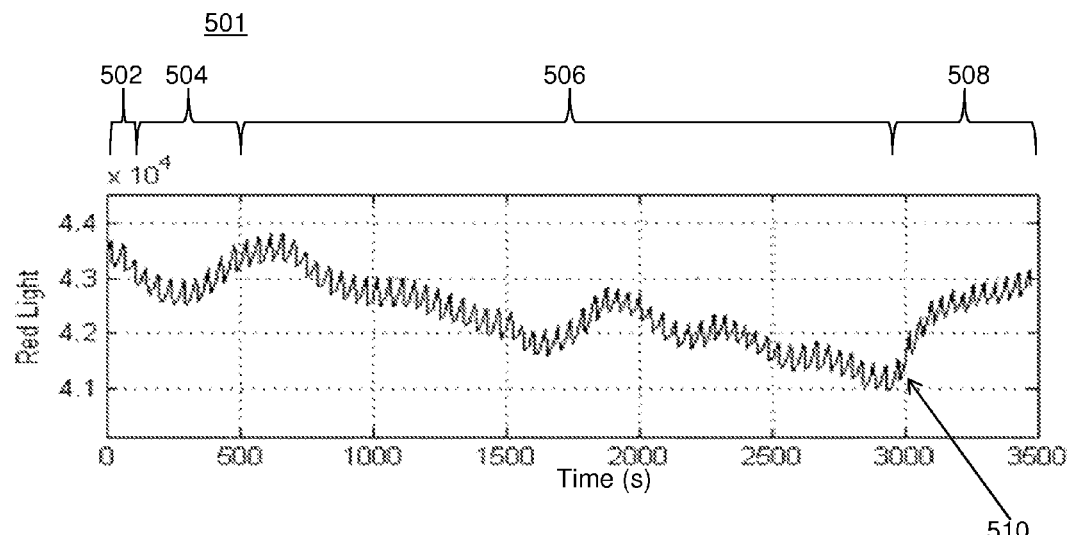

FIGS. 5A and 5B are exemplary graphs showing data sensed by the patient parameter sensor 300 of the controller 6 (FIGS. 1 and 3). FIG. 5A is a graphical representation 500 of an amount of pressure measured in millimeters of mercury (mmHg) in the pressure measurement chamber 4 over a period of time in seconds. During the time period indicated by reference numeral 502, the controller 6 signals the pressure source to pressurize the pressure measurement chamber (inflatable bladder) of a respective cuff in order to determine an intra-arterial pressure in a non-invasive manner. During the time period labeled 504, a pressure sensor in the controller 6 senses a pressure in the measurement chamber and selectively controls the pressure source to reduce the pressure in the chamber until the pressure in the chamber is equal to the pressure in the artery. For example, the pressure in the chamber is determined to be equal to a pressure within the artery using a calculation that relies on the light signal data detected by the detector. Without the light signal, it would not be possible to accurately reduce the pressure in the chamber to that of the artery. The blood volume in the finger arteries is measured using the light emitter and detector. The pulsation of the light reaching the light detector is directly related to the pulsation of blood in the finger arteries and corresponds to the cardiac cycle. At systole, the light absorption is stronger because there is more blood and less light reaches the detector, and at diastole the absorption is weaker, increasing the amount of light reaching the detector. The plethysmographic signal is then used for controlling the counter pressure in the cuff's inflatable bladder. In exemplary operation, during systole and using the average blood volume as a reference, when pulsatile blood volume increases in the finger, the controller increases the control point, and the cuff pressure is increased until the blood volume is decreased to the reference value by external pressure from the cuff. During diastole, when blood volume in the finger decreases, the controller lowers the control point, and therefore, the cuff pressure to the point where the blood volume reaches the reference point again. The plethysmograph therefore monitors the pulse and continuously controls the external pressure in the cuff so that the pressure in the cuff stays coupled with the pressure in the artery. Once a steady pressure is reached, the controller controls the pressure source to maintain the desired steady pressure level in order to measure arterial pressure data by passing light having a first wavelength through the finger on which the cuff is positioned. This measurement occurs continuously throughout time period 506. Time period 508 depicts depressurization of the chamber by the controller.

FIG. 5B is a graphical representation of the absorbance of red light (light having the first wavelength) emitted by an LED emitter. As can be seen herein, the amount of absorbed red light increases over time as the cuff remains pressurized resulting in decreased amount of red light being detected by a detector as time increases. The amount of light absorbed may be used to selectively control the operation of the apparatus to change which cuff of the cuff pair is pressurized at a given time. For example, if the light detected by detector falls below a threshold level indicated herein by reference numeral 510, the controller automatically determines that the decreased light detected may be caused by increased absorption of light by deoxygenated hemoglobin and may cause venous congestion. Thus, upon the detector detecting that the amount of light passing through the finger falls below threshold 510, the controller automatically causes the currently pressurized cuff to be depressurized and automatically pressurizes the other cuff of the cuff pair. This automatic depressurization is represented by time period 508 in FIG. 5A.

While the explanation of the single cuff feedback control mechanism is described with reference to the absorption of red light, one skilled in the art would understand that the result of the oxygen saturation data may be plotted and would yield a similar result thus causing the controller to automatically depressurize a first cuff and pressurize the second cuff.

Figure 6:
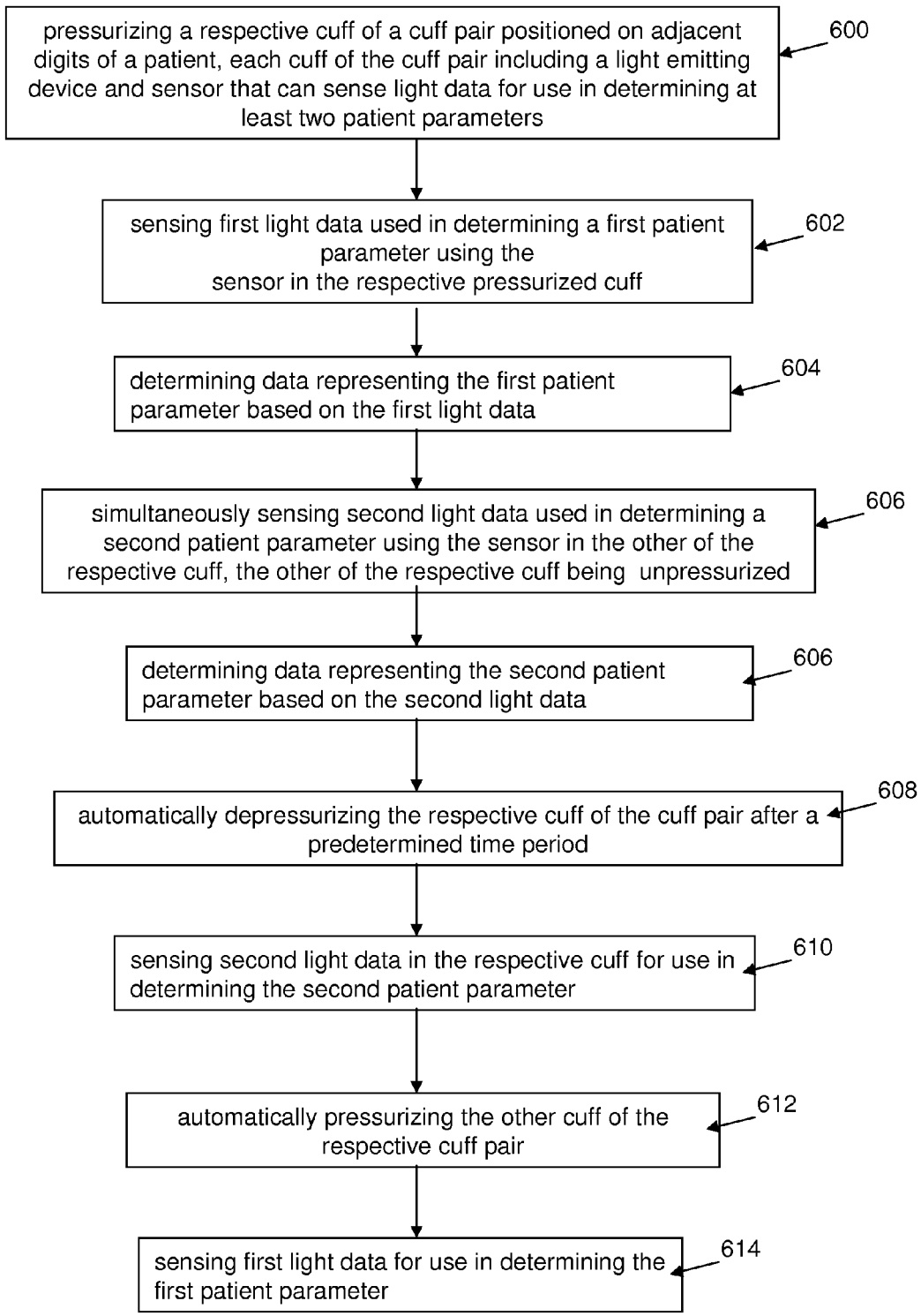
FIG. 6 is a flow diagram detailing the operation of the apparatus according to invention principles.

FIG. 6 is a flow diagram detailing an exemplary operation of the dual sensor apparatus in the first operational mode according to invention principles. In step 600, a respective cuff of a cuff pair positioned on adjacent digits of a patient is pressurized. Each cuff of the cuff pair includes a light emitting device and sensor that can sense light data for use in determining at least two patient parameters. First light data used in determining a first patient parameter is sensed in step 602 using the sensor in the respective pressurized cuff. In one embodiment, step 602 may include emitting a first type of light having a first wavelength from the light emitting device, passing the first type of light from the light source through a digit of a patient and detecting an amount of the first type of light that has been absorbed by the digit of the first patient. In step 604, data representing the first patient parameter is determined based on the first light data. In one embodiment this determination may be based on absorption data associated with an amount of light absorbed and provided to a processor.

Second light data used in determining a second patient parameter is sensed in step 606 using the sensor in the other cuff, the other cuff being unpressurized. In one embodiment, the activity of sensing in step 606 includes emitting a second type of light from a light source, the second type of light including a pulse of light having a first wavelength and a pulse of light having a second wavelength. Successive pulses of light having the first wavelength and second wavelength are passed through a digit of a patient and amounts of the second type of light that has been absorbed by the digit of the first patient are detected. Data representing the second patient parameter is determined based on the sensed second light data in step 608. In one embodiment, the determination made in step 608 may be based on absorption data sensed by the sensor and provided to a processor.

In step 610, the respective cuff of the cuff pair is automatically depressurized after a predetermined time period and second light data in the respective cuff is sensed in step 612 and used for determining the second patient parameter. In step 614, the other cuff of the respective cuff pair is automatically pressurized and first light data for use in determining the first patient parameter is sensed in step 616.

The adjustable dual cuff sensor apparatus advantageously employs a light emitter and corresponding sensor that is able to sense light data that may be used in automatically determining at least two patient parameters including intra-arterial blood pressure and blood oxygenation saturation levels. This is advantageously accomplished by sensing one of the parameters in a first cuff that is in a pressurized state and simultaneously sensing the other parameter in the second cuff that is not pressurized. The respective states of pressurization are alternated such that patient discomfort is minimized without disrupting patient parameter monitoring. This occurs by automatically switching the type of parameter being monitored by a respective cuff based on the pressurization state of the cuff. Additionally, the apparatus advantageously enables sensing and determining of both patient parameter values when a respective cuff is in a pressurized state, the data from the simultaneous intra-cuff determination may be used to further control operation of the apparatus.

While the invention is receptive to various modifications, and alternative forms, specific examples thereof have been shown in the drawings and are herein described in detail. It should be understood, however, that the invention is not limited to the particular forms or methods disclosed, but to the contrary, the invention is meant to cover all modifications, equivalents, and alternatives falling with the spirit and scope of the disclosed subject matter.

I claim:

1. An apparatus for combined continued non-invasive measurement of blood pressure and pulse oximetry, the apparatus comprising:
a first cuff including a first inflatable bladder, a first light emitting device and a first sensor that senses light data, the first cuff which can releasably receive a first finger on a first hand of a user for use in calculating at least a first patient parameter of a first type and a second patient parameter of a second type, said first type being different from said second type;
a second cuff including a second inflatable bladder, a second light emitting device and a second sensor that senses light data, the second cuff which can releasably receive a second finger on the first hand of the user for use in calculating the at least first and second patient parameters; and
a controller coupled to the first and second sensors, wherein the controller is configured to alternatingly cause the bladder of one of the first and second cuffs to inflate while the other is not pressurized, the sensor of the one of the first and second cuffs is configured to sense first light data, the first light data being received by said controller from the sensor, the controller being configured to derive said first patient parameter based on the first light data from the pressurized one of the first and second cuffs, the sensor of the other of the first and second cuffs is configured to simultaneously sense second light data used by said controller to determine said second patient parameter from the depressurized one of the first and second cuffs;
wherein said controller is configured to maintain the one of the first and second cuffs in a pressurized state for a predetermined duration and, at the expiration of the predetermined duration, to automatically depressurize the one of the first and second cuffs and to automatically pressurize the other of the first and second cuffs.

2. The apparatus as recited in claim 1, wherein said first and second light emitting devices emit a first type of light for use in calculating the first patient parameter and a second type of light for use in calculating the second patient parameter.

3. The apparatus as recited in claim 2, wherein
the first and second sensors each include a photodetector configured to detect an amount of the first type of light and the second type of light.

4. The apparatus of claim 2, wherein
the first type of light includes light emitted at a first wavelength and the second type of light includes sequential pulses of light having different wavelengths, a first pulse being the light emitted at the first wavelength and a second, sequential pulse being light emitted at a second different wavelength.

5. The apparatus of claim 2, wherein the first type of light is red light for use in calculating the first patient parameter and the second type of light includes red light and infrared light for use in calculating the second patient parameter.

6. The apparatus of claim 1, further comprising
a pressure source connected to respective inflatable bladders in respective first and second cuffs and configured to pressurize a respective one of the first and second cuffs upon receipt of a control signal generated by the controller.

7. The apparatus of claim 1, wherein
in response to depressurizing the one of the first and second cuffs, the controller is configured to automatically cause the first sensor in the one of the first and second cuffs to sense light data for use in calculating the second patient parameter, and
in response to pressurizing the other of the first and second cuffs, the controller is configured to automatically cause the second sensor to sense light data for use in calculating the first patient parameter.

8. The apparatus of claim 1, wherein
said controller is further configured to use the light data sensed by the first sensor to calculate said second patient parameter and to simultaneously calculate first and second patient parameters using the light data sensed by the first sensor in the one of the first and second cuffs that has been inflated.

9. The apparatus of claim 1, wherein
said controller causes the light emitting device in the one of the first and second cuffs to emit successive pulses of light, wherein a first pulse of light has a first wavelength and a second pulse of light has a second wavelength.

10. The apparatus of claim 9, wherein
the controller uses light data derived from the first pulse of light to calculate the first patient parameter, and uses light data derived from the second pulse of light, in conjunction with first pulse light data, to determine the second patient parameter.

11. The apparatus of claim 1, wherein
in response to determining data representing the second patient parameter in the one of the first and second cuffs, the controller at least one of (a) modifies a pressure level in the one of the first and second cuffs; (b) depressurizes the one of the first and second cuffs and pressurizes the other of the first and second cuffs; and (c) generates an alert signal indicating that the second patient parameter has reached a threshold level.

12. The apparatus as recited in claim 1, wherein
the first and second cuffs are formed from a non rigid material and are adjustably connected to respective adjacent digits of the patient.

13. The apparatus as recited in claim 1, wherein
the first and second patient parameters include data representing (a) an intra arterial blood pressure and (b) a blood oxygen saturation level.

14. The apparatus as recited in claim 1, wherein
the second cuff is positioned around a second finger adjacent the first finger on the first hand of the user.

15. A method for combined continued non-invasive simultaneously measurement of blood pressure and pulse oximetry, the method comprising:
pressuring alternatingly a respective cuff of a cuff pair positioned on adjacent digits of a patient while the other cuff is not pressurized such that one of the cuffs is always inflated or being inflated while the other cuff is deflated or being deflated, each cuff of the cuff pair including a light emitting device and sensor that can sense light data for use in determining a first patient parameter of a first type from the pressurized respective cuff and a second patient parameter of a second type from the depressurized respective cuff, said first type being different from said second type;
sensing first light data used in determining said first patient parameter using the sensor in the respective pressurized cuff and determining data representing the first patient parameter based on the first light data;
simultaneously sensing second light data used in determining said second patient parameter using the sensor in the other of the respective cuff, the other of the respective cuff being unpressurized and determining data representing the second patient parameter based on the second light data; and
outputting data representing the first and second patient parameters for use by a healthcare professional charged with monitoring the patient.

16. The method of claim 15, further comprising the activity of
automatically depressurizing the respective cuff of the cuff pair after a predetermined time period and sensing second light data in the respective cuff for use in determining the second patient parameter; and
automatically pressurizing the other cuff of the respective cuff pair and sensing first light data for use in determining the first patient parameter.

17. The method of claim 15, wherein the activity of sensing first light data further includes:
emitting a first type of light having a first wavelength from the light emitting device;
passing the first type of light from the light source through a digit of a patient;
detecting an amount of the first type of light that has been absorbed by the digit of the patient; and
providing absorption data to a processor for use in determining the first patient parameter.

18. The method of claim 15, wherein the activity of sensing second light data further includes:
emitting a second type of light from a light source, the second type of light including a pulse of light having a first wavelength and a pulse of light having a second wavelength;
passing successive pulses of light having the first wavelength and second wavelength through a digit of a patient;
detecting amounts of the second type of light that has been absorbed by the digit of the patient; and
providing absorption data to a processor for use in calculating the first patient parameter.

19. The method of claim 15, further comprising the activity of
simultaneously sensing first and second light data in the respective cuff of the cuff pair that is pressurized, and determining, by a controller, first and second patient parameter data based on respective sensed first and second light data.

20. The method as recited in claim 19, further comprising the activity of
using second patient parameter data determined from the respective cuff of the cuff pair to control a pressure level in the respective cuffs of the cuff pair.

21. An apparatus for combined continued non-invasive measurement of blood pressure and pulse oximetry, the apparatus comprising:
a first cuff including a first inflatable bladder, a first light emitting device emitting a first and second type of light, and a first sensor that senses first and second light data for use in calculating at least two patient parameters, the first cuff being configured to releasably receive a first finger on a first hand of a user;
a second cuff including a second inflatable bladder, a second light emitting device emitting the first and second types of light, and a second sensor that senses the first and second light data for use in calculating the at least two patient parameters, the second cuff being configured to releasably receive a second finger on the first hand of the user; and
a controller coupled to the first and second sensors, wherein the controller is configured to alternatingly cause the bladder of one of the first and second cuffs to inflate while the other is not pressurized such that one of the cuffs is always inflated or being inflated while the other cuff is deflated or being deflated, the sensor of the one of the first and second cuffs is configured to sense first light data, the first light data being received by said controller from the sensor, the controller being configured to derive said first patient parameter based on the first light data from the inflated one of the first and second cuffs, the sensor of the other of the first and second cuffs is configured to simultaneously sense second light data used by said controller to determine said second parameter from the deflated one of the first and second cuffs.

22. The apparatus of claim 21, wherein
the first type of light includes light emitted at a first wavelength and the second type of light includes sequential pulses of light having different wavelengths, a first pulse being the light emitted at the first wavelength and a second, sequential pulse being light emitted at a second different wavelength.

23. The apparatus of claim 21, wherein
in response to determining data representing the second patient parameter in the first cuff, the controller at least one of (a) modifies a pressure level in the first cuff; (b) depressurizes the first cuff; and (c) generates an alert signal indicating that the second patient parameter has reached a threshold level.

24. The apparatus as recited in claim 21, wherein
the first and second cuffs are formed from a non rigid material and are adjustably connected to respective adjacent digits of the patient.

25. The apparatus as recited in claim 21, wherein the first patient parameter represents an intra arterial blood pressure and the second parameter represents a blood oxygen saturation level.

26. An apparatus for combined continued non-invasive measurement of blood pressure and pulse oximetry, the apparatus comprising:
- a first cuff including a first inflatable bladder, a first light emitting device and a first sensor that senses light data, the first cuff being configured to releasably receive a first finger on a first hand of a user for use in calculating at least a first patient parameter of a first type and a second patient parameter of a second type, said first type being different from said second type;
- a second cuff including a second inflatable bladder, a second light emitting device and a second sensor that senses light data, the second cuff being configured to releasably receive a second finger on the first hand of the user for use in calculating the at least first and second patient parameters; and
- a controller coupled to the first and second sensors and configured to
  - (i) maintain, during a first time period, the first cuff in a pressurized state and the second cuff in a depressurized state, the first sensor sensing first light data used by the controller to determine the first patient parameter during the first time period, second sensor simultaneously sensing second light data used by the controller to determine the second patient parameter during the first time period, and
  - (ii) at an end of the first time period, automatically depressurize the first cuff, and pressurize the second cuff, and
  - (iii) maintain, during a second time period, the second cuff in a pressurized state and the first cuff in a depressurized state, the first sensor sensing first light data used by the controller to determine the second patient parameter during the second time period, and the second sensor simultaneously sensing second light data used by the controller to determine the first patient parameter during the second time period;

wherein in response to the depressurizing of the first cuff, the first light emitting device ceases emitting the first light data and the first sensor discontinues sensing the first light data and begins sensing light data used by the controller to determine the second patient parameter, and wherein in response to the pressurizing of the second cuff, second light emitting device ceases emitting the second light data and the second sensor discontinues sensing the second light data and begins sensing light data used by the controller to determine the first patient parameter.

* * * * *